(12) United States Patent
Klicek

(10) Patent No.: US 6,210,403 B1
(45) Date of Patent: *Apr. 3, 2001

(54) AUTOMATIC CONTROL FOR ENERGY FROM AN ELECTROSURGICAL GENERATOR

(75) Inventor: Michael S. Klicek, Boulder, CO (US)

(73) Assignee: Sherwood Services AG, Schaffhausen (CH)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/132,940

(22) Filed: Oct. 7, 1993

(51) Int. Cl.[7] ................................................ A61B 18/12
(52) U.S. Cl. ............................ 606/34; 606/38; 606/39; 606/40
(58) Field of Search .............................. 606/32, 34, 35, 606/37–42

(56) References Cited

U.S. PATENT DOCUMENTS

| | | |
|---|---|---|
| 2,827,056 | 3/1958 | Dagelman . |
| 3,964,487 | 6/1976 | Judson . |
| 3,980,085 | 9/1976 | Ikuno . |
| 4,092,986 | 6/1978 | Schneiderman . |
| 4,094,320 | 6/1978 | Newton et al. . |
| 4,188,927 | 2/1980 | Harris . |
| 4,321,926 | 3/1982 | Roge . |
| 4,372,315 | 2/1983 | Shapiro et al. . |
| 4,582,057 * | 4/1986 | Auth et al. .............................. 606/31 |
| 4,658,819 | 4/1987 | Harris et al. . |
| 4,727,874 * | 3/1988 | Bowers et al. .......................... 606/38 |
| 4,739,759 * | 4/1988 | Rexroth et al. ......................... 606/34 |
| 4,860,745 | 8/1989 | Farin et al. . |
| 5,167,658 * | 12/1992 | Ensslin . |

FOREIGN PATENT DOCUMENTS

| | | |
|---|---|---|
| 1099658 | 4/1959 | (DE) . |
| 2455174 | 5/1975 | (DE) . |
| 2540968 | 3/1977 | (DE) . |
| 2823291 | 11/1979 | (DE) . |
| 2946728 | 5/1981 | (DE) . |
| 3120102 | 12/1982 | (DE) . |
| 3510586 | 10/1986 | (DE) . |

* cited by examiner

Primary Examiner—David M. Shay

(57) ABSTRACT

An electrosurgical generator control responds to tissue impedance between active and return electrodes during desiccation. Active and return generator leads to supply energy and a user control sets the level of energy desired for electrosurgery. Voltage and current sensing circuits respond to high frequency energy in the leads to signal voltage and current in the leads. A multiplier receives the signals to calculate power. A clock sets units of time during for which power calculation. An integrator calculates the energy supplied through the leads per time unit. The user control sets a reference signal for the energy level desired. A correlation circuit receives the energy calculations from the integrator and the reference signal and provides a feedback signal to indicate when the energy calculation equals the user control setting for altering the generator supply of energy to the leads. A counter assesses the number of packets of energy delivered against a setting of the user control and the total energy delivered is a function of multiple packet sequences containing pulses wherein the time between the pulses is controlled by the user control. The method uses the automatic control in measuring impedance during tissue desiccation and altering the output of an electrosurgical generator.

19 Claims, 2 Drawing Sheets

AUTOMATIC CONTROL FOR ENERGY FROM AN ELECTROSURGICAL GENERATOR

FIELD OF THE INVENTION

An automatic control for an electrosurgical generator measures energy delivered and, in particular, permits the operation of the electrosurgical generator during electrosurgical tissue desiccation. Surgeons find that manual operation by hand or foot activated switching can cause excessive surgical energy delivery resulting in over drying the tissue at the surgical site.

Surgeons have tried to deal with energy application by adjusting the basic power level of the electrosurgical generator and using the hand or foot switch to control the power applied over time. Unfortunately, that technique often leads to unintended power delivery or undesired duration of power delivery to the surgical site. Surgeons also experience difficulty in repeatably and/or consistently desiccating tissue to the desired levels due to the limits of their human reaction time or machine response time when manual or foot activated switches are used for manual control. In addition, during endoscopic procedures, surgeons lose some visual and tactile indications of desiccation progression.

BACKGROUND OF THE INVENTION

As a result of manual operation problems, several attempts to provide automatic generator operation when surgical forceps contact patient tissue have been patented. U.S. Pat. No. 2,827,056, German patent 1,099,658, German patent 28 23 291 describe circuits which place a direct current potential across the surgical forceps. Placement of the forceps across patient tissue causes a small DC current to flow therethrough. Direct current flow causes activation of a relay circuit enabling the higher power radio frequency energy to flow into the patient's tissue for surgical effect. Selecting fixed resistance values, within the circuits, determine the tissue impedance level below which radio frequency energy activation occurs.

German Patent DE 25 40 968 describes a circuit which uses a low-frequency measurement current to determine relative patient tissue impedance; low frequency current flow within a specified amplitude range turns on generator high frequency power for surgical effect. That circuit also includes a time delay relay for controlling time between application of forceps to patient tissue and subsequent generator operation.

Subsequent patents addressed the need for automatic turn off capability during bipolar desiccation procedures. German patent DE 31 20 102 A1 describes a circuit which monitors the differential quotient (time derivative) of patient tissue impedance to determine when to turn off radio frequency power delivery; a point of zero time derivative is selected to turn off power delivery. German patent DE 29 46 728 A1 describes a circuit which turns radio frequency power off after an adjustable, but fixed time delay. German patent DE 35 10586 describes a circuit which uses a low-frequency control current or low level generator radio frequency current source and a current level monitor to turn on generator radio frequency power for surgical effect. The circuit also monitors the generator output voltage for third harmonic content generated when desiccation completes and sparking begins to cause harmonic frequency generation to turn off generator radio frequency power. It is a device which measures current flowing through the tissue and forms a digitized signal of current level. The signal and the manual activation are combined to operate the device.

U.S. Pat. No. 4,860,745 discusses the problems encountered when turning off radio frequency power based upon measurements of the time derivative of patient tissue impedance and, instead, presents a circuit which turns off generator radio frequency power based upon fixed fractional changes in the amount of radio frequency current delivered to the patient tissue during desiccation or based upon generator sparking and harmonic frequency generation. A peak detector circuit examines the peak current at the forceps and a second circuit which monitors the decreasing current during coagulation. Measured current levels are converted to voltages within the circuits. The voltages, thus measured, control the electrosurgical generator which is turned off when a fraction of the peak current is greater than the current measured which flows through the tissue during coagulation. If the current flowing through the tissue is greater than the fraction, then the output of the electrosurgical generator is continued until it is less.

German patent 2,455,174 is directed to a switch and relay so when the doctor operates the switch, which is normally closed; it enables ESU control. Opening the switch activates a relay which operates the electrosurgical generator when the impedance value between the forceps is within a predetermined range. These claims are avoided since we have no switch and relay. Also required is a manually activated switch to operate the relay. The switch is on the handle of the forceps.

U.S. Pat. No. 4,658,819 discloses a circuit wherein the power delivered to the electrode is a function of the voltage from a DC supply and the load as measured by sensors of load voltage and current. A microprocessor controller digitizes the sensing signals and computes the load impedance and actual power being delivered. The microprocessor controller accordingly repeats the measurement, calculation and correction process approximately as long as the generator is operating. U.S. Pat. No. 4,372,315 discloses a circuit which measures impedances after delivering a set number of radio frequency pulses on a pulse burst by pulse burst basis. U.S. Pat. No. 4,321,926 has a feedback system to control dosage but the impedance sensing is not on a real time basis. U.S. Pat. Nos. 3,964,487, 3,980,085, 4,188,927, and 4,092,986 have circuitry to reduce the output current in accordance with increasing load impedance. In those patents voltage output is maintained constant while the current is decreased with increasing load impedance. U.S. Pat. No. 4,094,320 has a circuit that responds to impedance changes as measured by sensing current in the active and return leads. The sensed currents are subtracted from one another and it that exceeds a variable threshold the generator is turned off. The variable threshold is a function of power level and leakage current through stray capacitance.

No circuitry has been known to automatically control the energy applied by comparing a basic user setting of power level desired to the actual power delivered over time. No automatic control is responsive to actual and desired energy delivery which are a function of tissue impedance. It is desired to provide consistent desiccation levels.

SUMMARY OF THE INVENTION

An automatic control for an electrosurgical generator responds to the level of tissue impedance between active and return electrodes of the electrosurgical generator during tissue desiccation. An electrosurgical generator preferably has an active lead and a return lead to supply high frequency electrosurgical energy, the electrosurgical generator may include a user control for setting the level of energy desired for electrosurgery. A voltage sensing circuit may respond to high frequency electrosurgical energy supplied by the electrosurgical generator and flowing through the leads. The voltage sensing circuit is preferably capable of providing a signal of voltage level between the active and return leads. A current sensing circuit may responds to high frequency electrosurgical energy supplied by the electrosurgical generator and flowing through the return lead, the current sensing circuit capable of providing a signal of current level. A multiplier receives the signals from the voltage and current sensing circuits and multiplies those signals together for preferably calculating the power flowing through the leads of the electrosurgical generator.

A clock may establish units of time during which power flow calculated by the multiplier is considered. An integrator most preferably calculates the energy supplied through the leads per each unit of time established by the clock based on the instantaneous power calculations of the multiplier. A user control may set a reference signal indicative of the energy level desired by the user. A correlation circuit preferably receives the energy calculations from the integrator and a reference signal in accord with the setting of the user control. The correlation circuit provides a feedback signal to indicate when the energy calculation equals the user control setting for altering the electrosurgical generator supply of high frequency electrosurgical energy to the active and return leads.

The correlation circuit is preferably a comparator to receive the energy calculations from the integrator and a reference signal in accord with the setting of the user control. The comparator provides a feedback signal to indicate when the energy calculation equals the user control setting for preferably terminating the electrosurgical generator supply of high frequency electrosurgical energy to the active and return leads. The correlation circuit may alternatively be a differential amplifier to receive the energy calculations from the integrator and a reference signal in accord with the setting of the user control. The differential amplifier provides a feedback quantity as a measure of the difference between the energy calculations and the user control setting for matching the electrosurgical generator supply of high frequency electrosurgical energy to the active and return leads.

The clock preferably sets units of time which are about a millisecond thus providing feedback in real time to the electrosurgical generator for regulating the electrosurgical generator supply of high frequency electrosurgical energy to the active and return leads. The integrator may calculate the energy applied over a unit of time or the area under the power curve of the electrosurgical generator for each unit of time during the operation of the electrosurgical generator during desiccation of tissue between the electrodes. A bipolar electrode is in one form of the control connected to the active and return leads. Monopolar electrodes are connected to the active and return leads in another iteration.

The electrosurgical generator output is preferably terminated by altering the drive circuit thereof so the supply of high frequency electrosurgical energy to the active and return leads is automatically adjusted. The user control may have two added adjusters one for the number of packets of energy and the other for a preset level of energy delivered per packet.

A counter may be in the electrosurgical generator to assess the number of packets of energy delivered against setting of the adjuster of the number of packets as established by the user control with a second comparator. The other adjuster for energy level per packet is preferably a potentiometer that provides a direct current voltage as the reference signal for energy level. The counter may be in the electrosurgical generator to assess the number of packets of energy delivered against setting of the adjuster of the number of packets as established by the user control with the second comparator and the total energy delivered is a function of multiple packet sequences containing pulses wherein the time between the pulses is controlled by the user control.

A method of automatic controlling an electrosurgical generator in response to the level of tissue impedance between active and return electrodes of the electrosurgical generator during tissue desiccation includes using an electrosurgical generator having an active lead and a return lead to supply high frequency electrosurgical energy. Setting a user control on the electrosurgical generator at the level of energy desired for electrosurgery is in the method. The method may have providing a signal of voltage level between the active and return leads with a voltage sensing circuit responsive to high frequency electrosurgical energy supplied by the electrosurgical generator and flowing through the leads. Also providing a signal of current level with a current sensing circuit responsive to high frequency electrosurgical energy supplied by the electrosurgical generator and flowing through the return lead is preferably another step. Then calculating the power flowing through the leads of the electrosurgical generator with a multiplier receiving the signals from the voltage and current sensing circuits and to multiply those signals together is the next step. The method may require establishing units of time with a clock during the time which power flow calculated by the multiplier is considered. The step of calculating with an integrator the energy supplied through the leads per each unit of time established by the clock based on the instantaneous power calculations of the multiplier follows. Then the step of setting with a user control a reference signal indicative of the energy level desired by the user continues the automatic control. Finally providing, with a correlation circuit connected to receive the energy calculations from the integrator and the reference signal in accord with the setting of the user control, a feedback signal to indicate when the energy calculation equals the user control setting allows for the step of altering the electrosurgical generator supply of high frequency electrosurgical energy to the active and return leads in accord with the feedback signal.

DETAILED DESCRIPTION OF THE INVENTION

Figure 1:
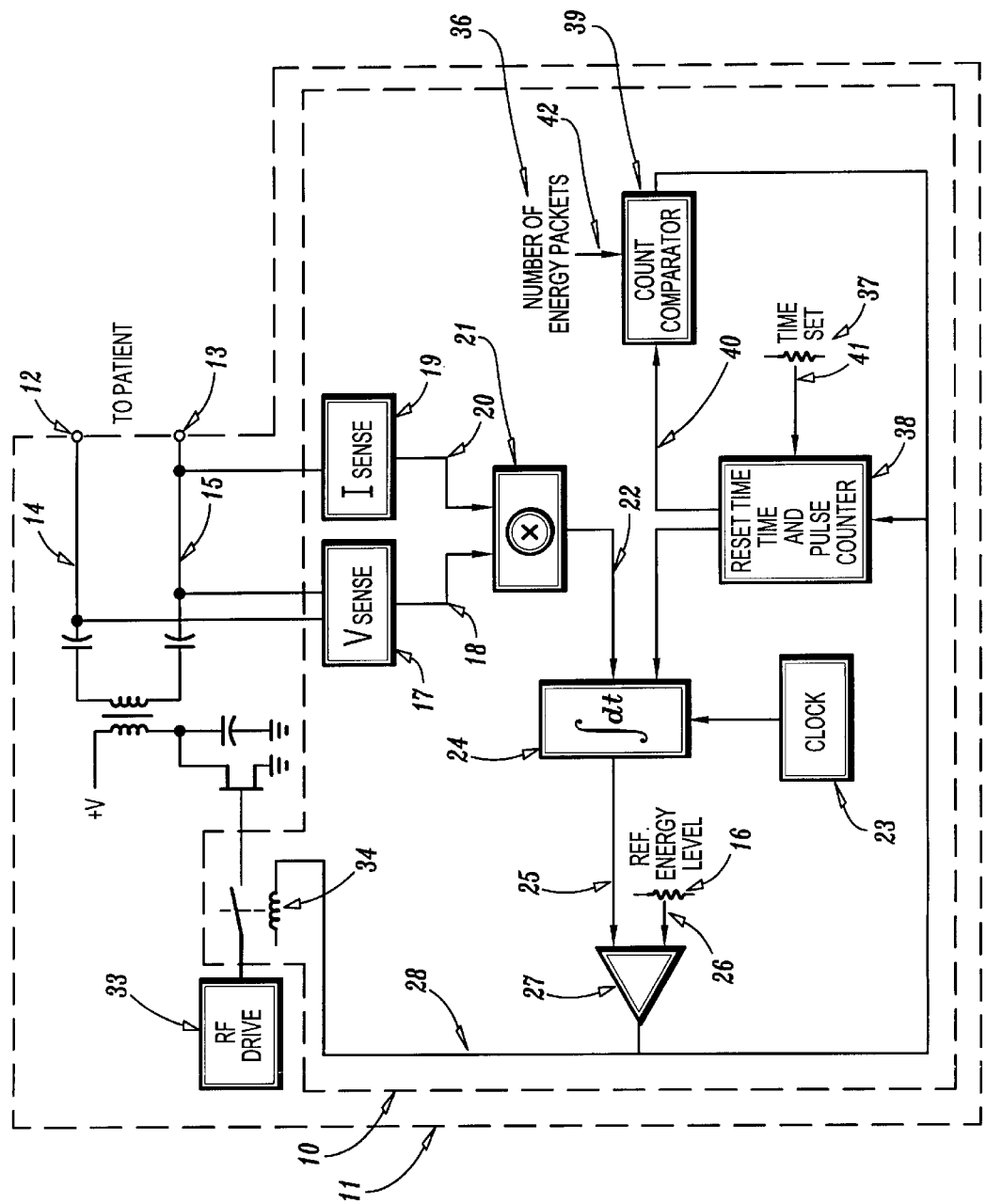
FIG. 1 is a circuit diagram in schematic form of the automatic control for energy supplied to the patient's tissue by an electrosurgical generator which is responsive to impedance changes between electrodes during tissue desiccation with a comparator.

An automatic control 10 for an electrosurgical generator 11 responds to the level of tissue impedance between active and return electrodes 12 and 13 of the electrosurgical generator 11 during tissue desiccation. An electrosurgical generator 11 such as the Force 40 manufactured and sold by Valleylab, Boulder, Colo. has an active lead 14 and a return lead 15 to supply high frequency electrosurgical energy. The electrosurgical generator 11 includes a user control 16 preferably on its front panel accessible to the doctor for setting the level of energy desired for electrosurgery. A voltage sensing circuit 17, has an isolation transformer which acts as an inductive pickup with its primary connected between the leads 14 and 15 induces the secondary windings to provide a voltage level signal 18 and thus, responds to high frequency electrosurgical energy supplied by the electrosurgical generator 11 and flowing through the leads 14 and 15. The voltage sensing circuit 17 is capable of providing the voltage level signal 18, in the form of a direct current voltage that varies, indicative of instantaneous voltage between the active and return leads 14 and 15. A current sensing circuit 19 responds to high frequency electrosurgical energy supplied by the electrosurgical generator 11 and flowing through the return lead 1 5. The preferred current sensing circuit 19, made by Pulse Engineering San Diego, Calif., model PE-51687, is capable of providing a signal of current level 20 instantaneously passing therethrough and the current level signal 20 is in the form of a direct current voltage that varies. The preferred analogue multiplier 21 is supplied by Analog Devices, AD534, Norwood, Mass., receives the instantaneous signals 18 and 20 from the voltage and current sensing circuits 17 and 19 and multiplies those signals 18 and 20 together for calculating the instantaneous power 22 flowing through the leads of the electrosurgical generator 11.

A clock 23, including a crystal oscillator and a frequency divider, establishes units of time during which power flow calculated by the multiplier 21 is considered. An integrator 24 which is a high speed amplifier, from Analog Devices, AD380, Norwood, Mass., calculates the energy 25 supplied through the leads 14 and 15 per each unit of time established by the clock 23 based on the instantaneous power 22 calculations of the multiplier 21.

The user control 1 6 may be in the form of a knob, slider or the like and positioned on the front panel of the electrosurgical generator 11 (not shown) for use by the doctor to set a reference signal 26 indicative of the energy level desired. A correlation circuit 27 preferably receives the energy 25 as calculated from the integrator 24 and the reference signal 26 in accord with the setting of the user control 16. The correlation circuit 27 provides a feedback signal 28 to indicate when the energy 25 calculation equals the user control energy setting 26 for altering the electrosurgical generator 11 supply of high frequency electrosurgical energy to the active and return leads 14 and 15.

FIG. 1 is a circuit diagram in schematic form of the automatic control 10 for energy supplied to the patient's tissue by an electrosurgical generator 11 which is responsive to impedance changes between electrodes 12 and 13 during tissue desiccation. The correlation circuit 27 is preferably a comparator to receive the energy 25 calculated from the integrator 24 and the reference signal 26 in accord with the setting of the user control 16. The comparator 27 provides the feedback signal 28 to indicate when the energy 25 calculated equals the user control energy setting 26 for preferably terminating the electrosurgical generator supply of high frequency electrosurgical energy to the active and return leads 14 and 15.

Figure 2:
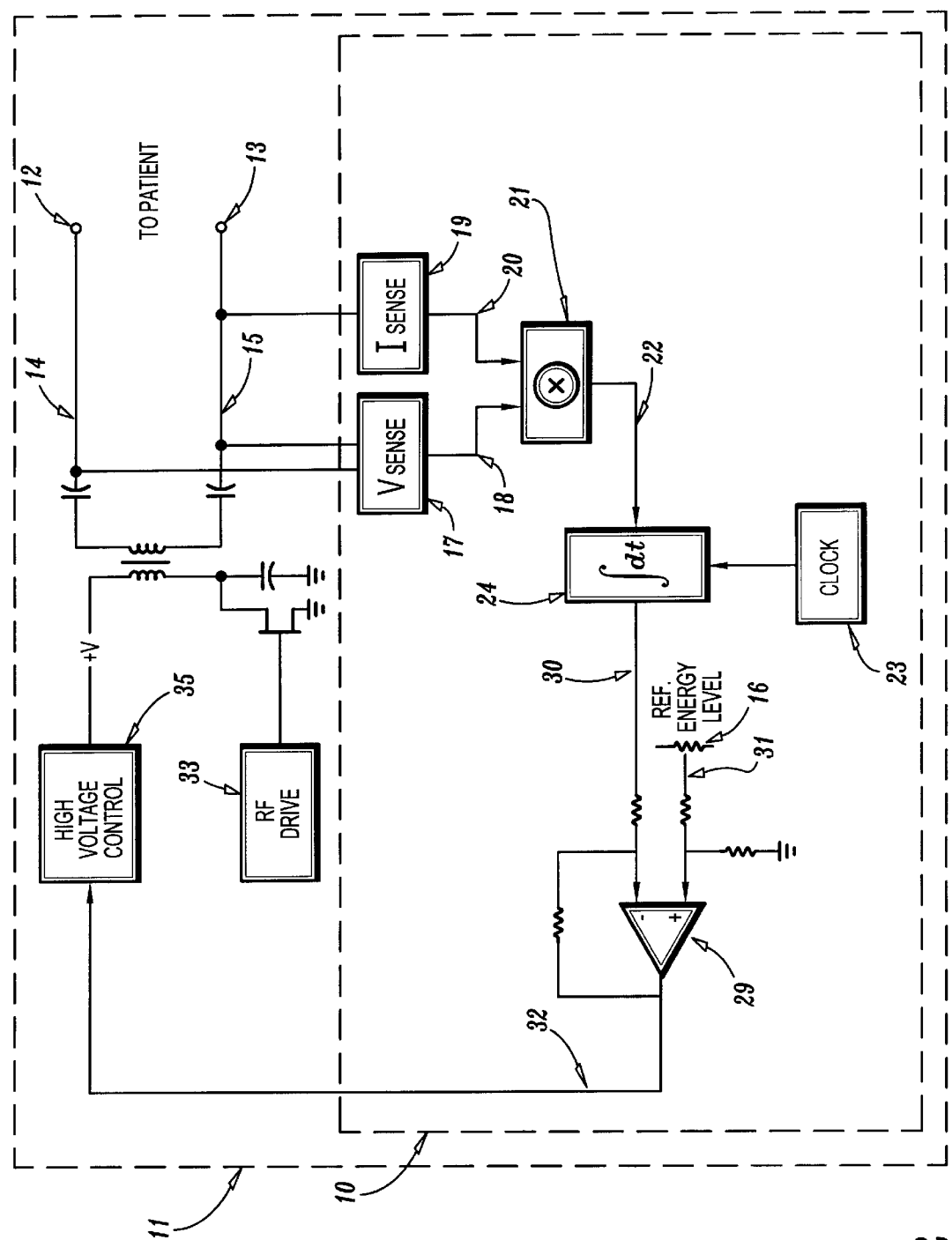
FIG. 2 is an alternate circuit diagram in schematic form of the automatic control for energy supplied to the patient's tissue by an electrosurgical generator which is responsive to impedance changes between electrodes during tissue desiccation with a differential amplifier.

FIG. 2 is an alternate circuit diagram in schematic form of the automatic control 10 for energy supplied to the patient's tissue by an electrosurgical generator 11 which is responsive to impedance changes between electrodes 12 and 13 during tissue desiccation with a differential amplifier 29. The correlation circuit may alternatively have the differential amplifier 29 to receive the energy 30 calculated from the integrator 24 and the reference signal 31 in accord with the setting of the user control 16. The differential amplifier 29 provides a feedback quantity 32 as a measure of the difference between the energy 30 calculated and the user control 16 energy 31 setting for matching the electrosurgical generator 11 supply of high frequency electrosurgical energy to the active and return leads 14 and 15.

The clock 23 preferably sets units of time which are about a millisecond thus providing the feedback quantity 32 in real time to the electrosurgical generator 11 for regulating the electrosurgical generator 11 supply of high frequency electrosurgical energy to the active and return leads 14 and 15. The integrator 24 may be in this alternate embodiment a part of a microprocessing unit such as the 80C652 from Signetics, Sunneyvale, Calif. The integrator 24 calculates the instantaneous energy 30 applied over a unit of time or the area under the power curve (not shown) of the electrosurgical generator 11 for each unit of time during the operation of the electrosurgical generator 11 as tissue is desiccated between the electrodes 12 and 13.

Tissue desiccation can be accomplished many ways with electrosurgery and monopolar and bipolar tools are available to treat tissue and produce the desiccating electrosurgical effect. A bipolar electrode may be connected to the active and return leads 14 and 15 in one form of the automatic control 10. Monopolar electrodes are connected to the active and return leads 14 and 15 in another iteration. Typically the major differences between monopolar and bipolar tools is the common support for the similarly sized electrodes used in bipolar such that the electrodes 12 and 13 are juxtaposed in position to grasp tissue therebetween. In monopolar configurations the electrodes 12 and 13 are typically separated and thus independently supported with a smaller active electrode at the surgical site and a larger return electrode on external tissue.

The electrosurgical generator 11 output is preferably terminated by altering the drive circuit 33 thereof in FIGS. 1 and 2 so the supply of high frequency electrosurgical energy to the active and return leads 14 and 15 is automatically adjusted. FIG. 1 includes a relay 34 to disconnect and reconnect the power from the drive circuit 33. In FIG. 2 a high voltage control 35 regulates the output.

The user control 16 in one alternative, e.g. FIG. 1, may have two added adjusters 36 and 37, one for the number of packets of energy supplied 36 to the active and return leads 14 and 15 and the other 37 for setting a preset level time between the packets of energy delivered. A counter 38 such as the 74LS190 from Texas Instruments, Dallas, Tex. is in the electrosurgical generator 11 to assess with a second comparator 39, such as 74LS85 from Texas Instrument, Dallas the number of packets of energy 40 delivered against setting of the adjuster of the number of packets 36. The other adjuster 37 for time between energy packet is in the preferred embodiment of FIG. 1, a potentiometer that provides a direct current voltage as the reference signal 41 for time between packets. The counter 38 is easily made a part of the electrosurgical generator 11 so assessment of the number of packets of energy 40 delivered against the setting of the adjuster 36 of the number of packets desired 42, as established by the adjuster 36, will control the total energy delivered by the multiple packet sequences which each contain pulses. The time between the pulses is controlled by the adjuster 37.

A method of automatic controlling the electrosurgical generator 11 in response to the level of tissue impedance between active and return electrodes 12 and 13 of the electrosurgical generator 11 during tissue desiccation includes using the electrosurgical generator 11 having active and return leads 14 and 15 that supply high frequency electrosurgical energy. Setting the user control 16 on the electrosurgical generator 11 at the level of energy desired, either 31 or 26, for electrosurgery is in the method. The method includes providing the signal of voltage level 18 between the active and return leads 14 and 15 with the voltage sensing circuit 17 responsive to high frequency electrosurgical energy supplied by the electrosurgical generator 11 between the leads 14 and 15. Also providing a signal 20 of current level with the current sensing circuit 17 responsive to high frequency electrosurgical energy supplied by the electrosurgical generator 11 and flowing through the return lead 15 is a further step. Then calculating the power 22 flowing through the leads 14 and 15 of the electrosurgical generator 11 with the multiplier 21 receiving the signals 18 and 20 from the voltage and current sensing circuits 17 and 19 and by multiplying those signals 18 and 20 together is the next step. The method requires establishing units of time with the clock 23 during which the time for power 22 flowing is calculated by the multiplier 21. The step of calculating with the integrator 24 the energy 24 or 30 supplied through the leads 14 and 15 per each unit of time established by the clock 23 and based on the instantaneous power 22 calculations of the multiplier 21 follows. The step of setting with the user control 16 a reference signal 26 or 31 indicative of the energy level desired by the user gives a datum to which the automatic control is regulated. Finally providing, with the correlation circuit 27 or 29 connected to receive the energy calculations 25 or 30 from the integrator 24 and the reference signal 26 or 31 in accord with the setting of the user control 16, the feedback signal 28 or 32 to indicate when the energy calculation equals the user control setting 26 and 31. Altering the electrosurgical generator 11 supply of high frequency electrosurgical energy to the active and return leads 14 and 15 in accord with the feedback signal 28 or 32 is the controlling step of the method.

In FIGS. 1 and 2 the high voltage control and the drive for the high frequency output are altered respectively. In the latter the drive can be terminated.

What is claimed is:

1. An electrosurgical generator responsive to levels of tissue impedance between an active electrode and a return electrode wherein each electrode is electrically connected to the electrosurgical generator comprising:

an active lead and a return lead, each electrically connected to the electrosurgical generator to supply high frequency electrosurgical energy in the form of at least one energy packet;

a user control, electrically connected to the electrosurgical generator, for setting a preset level of energy desired for electrosurgery and for setting a reference signal in the electrosurgical generator indicative of the preset energy level desired by the user; said user control further comprising a first adjuster for setting a total number of energy packets and a second adjuster for setting a time between delivery of energy packets;

an automatic control circuit, electrically connected to the electrosurgical generator;

a voltage sensing circuit, within the automatic control circuit, responsive to high frequency electrosurgical energy supplied by the electrosurgical generator and flowing through the leads, the voltage sensing circuit capable of providing a signal of voltage level between the active and return leads;

a current sensing circuit, within the automatic control circuit, responsive to high frequency electrosurgical energy supplied by the electrosurgical generator and flowing through the return lead, the current sensing circuit capable of providing a signal of current level;

a multiplier, within the automatic control circuit, connected to the voltage and current sensing circuits to receive the signals from the voltage and current sensing circuits and to multiply those signals together for calculating power flow through the leads of the electrosurgical generator;

a clock, within the automatic control circuit, connected to the multiplier and the electrosurgical generator, the clock for establishing units of time during which power flow calculated by the multiplier is considered;

an integrator, within the automatic control circuit, joined to the multiplier and the clock and responsive thereto, the integrator to calculate an amount of energy supplied through the leads per each unit of time established by the clock based on power flow calculations of the multiplier, and a correlation circuit, within the automatic control circuit, coupled to the integrator to receive the amount of energy calculated from the integrator and the reference signal in accord with the setting of the user control to which the correlation circuit is connected, the correlation circuit electrically connected to the electrosurgical generator to provide a feedback signal to indicate when the amount energy calculated equals the reference signal of the user control setting for altering the electrosurgical generator supply of high frequency electrosurgical energy to the active and return leads responsive to impedance changes between active and return electrodes during tissue desiccation.

2. The electrosurgical generator responsive to the level of tissue impedance between active and return electrodes of the electrosurgical generator of claim 1 wherein a comparator in the correlation circuit is connected to receive the energy calculations from the integrator and the reference signal in accord with the setting of the user control, the comparator to provide the feedback signal to indicate when the energy calculation equals the user control setting for terminating the electrosurgical generator supply of high frequency electrosurgical energy to the active and return leads so the supply of high frequency is automatically adjusted.

3. The electrosurgical generator responsive to the level of tissue impedance between active and return electrodes of the electrosurgical generator of claim 1 wherein a differential amplifier in the correlation circuit is connected to receive the energy calculations from the integrator and reference signal in accord with the setting of the user control, the differential amplifier to provide feedback quantity as a measure of the difference between the energy calculations and the user control setting for matching the electrosurgical generator supply of high frequency electrosurgical energy to the active and return leads is automatically adjusted in accord with the feedback quantity to narrow the difference between the energy calculations and the setting of the user control.

4. The electrosurgical generator responsive to the level of tissue impedance between active and return electrodes of the electrosurgical generator of claim 1 wherein the clock has structure that sets units of time which are about a millisecond thus providing feedback useful for immediate use in real time to the electrosurgical generator for regulating the electrosurgical generator supply of high frequency electrosurgical energy to the active and return leads.

5. The electrosurgical generator responsive to the level of tissue impedance between active and return electrodes of the electrosurgical generator of claim 1 wherein the electrosurgical generator output is terminated in response to said feedback signal by altering a drive circuit in the electrosurgical generator thereof so the supply of high frequency electrosurgical energy to the active and return leads is terminated.

6. The electrosurgical generator responsive to the level of tissue impedance between active and return electrodes of the electrosurgical generator of claim 1 wherein the integrator has a place therein that calculates the energy applied over each unit of time established by the clock during the operation of the electrosurgical generator.

7. The electrosurgical generator responsive to the level of tissue impedance between active and return electrodes of the electrosurgical generator of claim 6 wherein a bipolar electrode configuration connects the active and return leads for use on the tissue.

8. The electrosurgical generator responsive to the level of tissue impedance between active and return electrodes of the electrosurgical generator of claim 6 wherein a monopolar electrode is connected to the active lead for use on the tissue.

9. An electrosurgical generator responsive to levels of tissue impedance between an active electrode and a return electrode wherein each electrode is electrically connected to the electrosurgical generator comprising:

an active lead and a return lead wherein each electrically connected to the electrosurgical generator to supply high frequency electrosurgical energy;

a user control, electrically connected to the electrosurgical generator, for setting a preset level of energy desired for electrosurgery and for setting a reference signal in the electrosurgical generator indicative of the preset energy level desired by the user;

an automatic control circuit, electrically connected to the electrosurgical generator;

a voltage sensing circuit, within the automatic control circuit, responsive to high frequency electrosurgical energy supplied by the electrosurgical generator and flowing through the leads, the voltage sensing circuit capable of providing a signal of voltage level between the active and return leads;

a current sensing circuit, within the automatic control circuit, responsive to high frequency electrosurgical energy supplied by the electrosurgical generator and flowing through the return lead, the current sensing circuit capable of providing a signal of current level;

a multiplier, within the automatic control circuit, connected to the voltage and current sensing circuits to receive the signals from the voltage and current sensing circuits and to multiply those signals together for calculating power flow through the leads of the electrosurgical generator;

a clock, within the automatic control circuit, connected to the multiplier and the electrosurgical generator, the clock for establishing units of time during which power flow calculated by the multiplier is considered;

an integrator, within the automatic control circuit, joined to the multiplier and the clock and responsive thereto, the integrator to calculate an amount of energy supplied through the leads per each unit of time established by the clock based on power flow calculations of the multiplier;

a correlation circuit, within the automatic control circuit, coupled to the integrator to receive the amount of energy calculated from the integrator and the reference signal in accord with the setting of the user control to which the correlation circuit is connected, the correlation circuit electrically connected to the electrosurgical generator to provide a feedback signal to indicate when the amount energy calculated equals the reference signal of the user control setting for altering the electrosurgical generator supply of high frequency electrosurgical energy to the active and return leads responsive to impedance changes between active and return electrodes during tissue desiccation; and wherein the user control has two added adjusters one for setting a number of packets of energy and another for setting a preset level of energy delivered per packet.

10. The electrosurgical generator responsive to the level of tissue impedance between active and return electrodes of the electrosurgical generator of claim 9 wherein a counter in the electrosurgical generator assesses the number of packets of energy delivered against the setting of the one adjuster of the number of packets, as established by the user control, with a second comparator.

11. The electrosurgical generator responsive to the level of tissue impedance between active and return electrodes of the electrosurgical generator of claim 9 wherein the adjuster for energy level per packet includes a potentiometer that provides a direct current voltage as the reference signal of energy level.

12. The electrosurgical generator responsive to the level of tissue impedance between active and return electrodes of the electrosurgical generator of claim 10 wherein the counter in the electrosurgical generator assesses the number of packets of energy delivered against the setting of the adjuster of the number of packets as established by the user control with the second comparator and the total energy delivered is a function of multiple packet sequences containing pulses wherein the time between the pulses is controlled by the user control.

13. An electrosurgical generator setting responsive to levels of tissue impedance between an active electrode and a return electrode wherein each electrode is electrically connected to the electrosurgical generator comprising:

an active lead and a return lead wherein each electrically connected to the generator to supply high frequency electrosurgical energy in the form of at least one energy packet;

a user control, electrically connected to the electrosurgical generator, for a preset level of energy desired for electrosurgery and for setting a reference signal in the electrosurgical generator indicative of the preset energy level desired by the user; said user control further comprising a first adjuster for setting a total number of energy packets and a second adjuster for setting a time between delivery of energy packets;

an automatic control circuit, electrically connected to the electrosurgical generator;

a voltage sensing circuit, within the automatic control circuit, responsive to high frequency electrosurgical energy supplied by the electrosurgical generator and flowing through the leads, the voltage sensing circuit capable of providing a signal of voltage level between the active and return leads;

a current sensing circuit, within the automatic control circuit, responsive to high frequency electrosurgical energy supplied by the electrosurgical generator and flowing through the return lead, the current sensing circuit capable of providing a signal of current level;

a multiplier, within the automatic control circuit, connected to the voltage and current sensing circuits to receive the signals from the voltage and current sensing circuits and to multiply those signals together for calculating power flow through the leads of the electrosurgical generator;

a clock, within the automatic control circuit, for establishing units of time during which power flow calculated by the multiplier is considered, the clock connected to the multiplier and the electrosurgical generator for setting units of time which are about a millisecond for thus providing feedback useful for immediate use in real time to the electrosurgical generator for regulating the electrosurgical generator supply of high frequency electrosurgical energy to the active and return leads;

an integrator, within the automatic control circuit, joined to the multiplier and clock and responsive thereto, the integrator to calculate an energy supplied through the leads per each unit of time established by the clock based on an instantaneous power flow calculation of the multiplier, the integrator for calculating the energy applied over each unit of time during the operation of the electrosurgical generator during desiccation of tissue between the electrodes, and a correlation circuit, within the automatic control circuit, coupled to the integrator to receive amount of energy calculated from the integrator and the reference signal in accord with the setting of the user control to which the correlation circuit is connected, the correlation circuit electrically connected to the electrosurgical generator to provide a feedback signal to indicate when the amount of energy calculated equals the user control setting for altering the electrosurgical generator supply of high frequency electrosurgical energy to the active and return leads and wherein the correlation circuit is a comparator to receive the energy calculations from the integrator and a reference signal in accord with the setting of the user control, the comparator to provide a feedback signal to indicate when the amount of energy calculated equals the user control setting for terminating the electrosurgical generator supply of high frequency electrosurgical energy to the active and return leads by altering a drive circuit thereof so the supply of high frequency electrosurgical energy to the active and return leads is automatically adjusted.

14. An electrosurgical generator setting responsive to levels of tissue impedance between an active electrode and a return electrode wherein each electrode is electrically connected to the electrosurgical generator comprising:

an active lead and a return lead wherein each electrically connected to the generator to supply high frequency electrosurgical energy;

a user control, electrically connected to the electrosurgical generator, for a preset level of energy desired for electrosurgery and for setting a reference signal in the electrosurgical generator indicative of the preset energy level desired by the user, an automatic control circuit, electrically connected to the electrosurgical generator;

a voltage sensing circuit, within the automatic control circuit, responsive to high frequency electrosurgical energy supplied by the electrosurgical generator and flowing through the leads, the voltage sensing circuit capable of providing a signal of voltage level between the active and return leads;

a current sensing circuit, within the automatic control circuit, responsive to high frequency electrosurgical energy supplied by the electrosurgical generator and flowing through the return lead, the current sensing circuit capable of providing a signal of current level;

a multiplier, within the automatic control circuit, connected to the voltage and current sensing circuits to receive the signals from the voltage and current sensing circuits and to multiply those signals together for calculating power flow through the leads of the electrosurgical generator;

a clock, within the automatic control circuit, for establishing units of time during which power flow calculated by the multiplier is considered, the clock connected to the multiplier and the electrosurgical generator for setting units of time which are about a millisecond for thus providing feedback useful for immediate use in real time to the electrosurgical generator for regulating the electrosurgical generator supply of high frequency electrosurgical energy to the active and return leads;

an integrator, within the automatic control circuit, joined to the multiplier and clock and responsive thereto, the integrator to calculate an energy supplied through the leads per each unit of time established by the clock based on an instantaneous power flow calculation of the multiplier, the integrator for calculating the energy applied over each unit of time during the operation of the electrosurgical generator during desiccation of tissue between the electrodes;

a correlation circuit, within the automatic control circuit, coupled to the integrator to receive amount of energy calculated from the integrator and the reference signal in accord with the setting of the user control to which the correlation circuit is connected, the correlation circuit electrically connected to the electrosurgical generator to provide a feedback signal to indicate when the amount of energy calculated equals the user control setting for altering the electrosurgical generator supply of high frequency electrosurgical energy to the active and return leads and wherein the correlation circuit is a comparator to receive the energy calculations from the integrator and a reference signal in accord with the setting of the user control, the comparator to provide a feedback signal to indicate when the amount of energy calculated equals the user control setting for terminating the electrosurgical generator supply of high frequency electrosurgical energy to the active and return leads by altering a drive circuit thereof so the supply of high frequency electrosurgical energy to the active and return leads is automatically adjusted; and wherein the user control has two added adjusters one for setting a number of packets of energy and another for setting the preset level of energy delivered per packet.

15. The electrosurgical generator responsive to the level of tissue impedance between active and return electrodes of the electrosurgical generator of claim 14 wherein the adjuster for energy level per packet includes a potentiometer that provides a direct current voltage as the reference signal of energy level.

16. The electrosurgical generator responsive to the level of tissue impedance between active and return electrodes of the electrosurgical generator of claim 14 wherein a counter in the electrosurgical generator assesses the number of packets of energy delivered against the setting of the one adjuster of the number of packets as established by the user control with a second comparator.

17. The electrosurgical generator responsive to the level of tissue impedance between active and return electrodes of the electrosurgical generator of claim 16 wherein the counter in the electrosurgical generator assesses the number of packets of energy delivered against the setting of the adjuster of the number of packets as established by the user control with the second comparator and the total energy delivered is a function of multiple packet sequences containing pulses wherein the time between the pulses is controlled by the user control.

18. A method of automatically controlling an electrosurgical generator in response to the level of tissue impedance between active and return electrodes of the electrosurgical generator during tissue desiccation includes the steps of:

using an electrosurgical generator having an active lead and a return lead to supply high frequency electrosurgical energy in the form of at least one energy packet to an active electrode and a return electrode;

setting a user control on the electrosurgical generator at an amount of energy desired for electrosurgery;

setting a first adjuster to a total number of energy packets to be supplied to said active electrode and said return electrode;

setting a second adjuster to a time between delivery of energy packets;

providing a signal of voltage level between the active and return leads with a voltage sensing circuit responsive to high frequency electrosurgical energy supplied by the electrosurgical generator and flowing through the leads;

providing a signal of current level with a current sensing circuit responsive to high frequency electrosurgical energy supplied by the electrosurgical generator and flowing through the active or return lead;

calculating power flow through the leads of the electrosurgical generator with a multiplier receiving the signals from the voltage and current sensing circuits by multiplying those signals together;

establishing units of time with a clock during a time during which power flow calculated by the multiplier is considered;

calculating with an integrator an energy supplied through the leads per each unit of time established by the clock based on an instantaneous power calculation of the multiplier;

setting with the user control a reference signal indicative of the amount of energy desired by the user;

providing, with a correlation circuit connected to receive energy calculated from the integrator, the reference signal in accord with the setting of the user control, and a feedback signal to indicate when the energy calculation equals the user control setting, and altering the electrosurgical generator supply of high frequency electrosurgical energy to the active and return leads in accord with the feedback signal.

19. An electrosurgical generator responsive to levels of tissue impedance comprising:

an active lead and a return lead wherein each lead is electrically coupled to said electrosurgical generator for supplying high frequency electrosurgical energy in the form of at least one energy packet;

a user control, electrically coupled to said electrosurgical generator, for setting a preset level of energy desired for electrosurgery and for setting a reference signal in said electrosurgical generator indicative of said preset energy level desired by a user, said user control comprising a first adjuster for setting a number of packets of energy and a second adjuster for setting a preset level of energy delivered per packet;

circuitry, electrically coupled to said active lead and said return lead, for calculating power flow through said active and return leads;

an integrator coupled to said circuitry for calculating an amount of energy supplied through said leads, per unit of time, based on said calculated power flow; and, a correlation circuit, coupled to said integrator to receive said calculation of an amount of energy from said integrator, and coupled to said user control to receive said reference signal, said correlation circuit providing a feedback signal to indicate when said calculation of an amount of energy equals said reference signal for terminating the supply high frequency electrosurgical energy to the active and return leads.

* * * * *